(12) United States Patent
Kamine

(10) Patent No.: US 11,751,972 B2
(45) Date of Patent: Sep. 12, 2023

(54) METHODS AND SYSTEMS FOR REMOTE AUGMENTED REALITY COMMUNICATION FOR GUIDED SURGERY

(71) Applicant: Tovy Kamine, Longmeadow, MA (US)

(72) Inventor: Tovy Kamine, Longmeadow, MA (US)

(73) Assignee: Tovy Kamine, Longmeadow, MA (US)

( * ) Notice: Subject to any disclaimer, the term of this patent is extended or adjusted under 35 U.S.C. 154(b) by 44 days.

(21) Appl. No.: 17/373,196

(22) Filed: Jul. 12, 2021

(65) Prior Publication Data

US 2021/0383612 A1    Dec. 9, 2021

Related U.S. Application Data

(63) Continuation of application No. 16/891,229, filed on Jun. 3, 2020, now Pat. No. 11,087,557.

(51) Int. Cl.
```
A61B 90/00    (2016.01)
G06T 19/00    (2011.01)
G06F 3/01     (2006.01)
G06T 7/70     (2017.01)
G06F 18/24    (2023.01)
G06V 10/74    (2022.01)
G06V 10/764   (2022.01)
G06V 20/20    (2022.01)
H04L 67/12    (2022.01)
```
(52) U.S. Cl.
CPC .............. *A61B 90/37* (2016.02); *A61B 90/36* (2016.02); *G06F 3/011* (2013.01); *G06F 18/24* (2023.01); *G06T 7/70* (2017.01); *G06T 19/006* (2013.01); *G06V 10/761* (2022.01); *G06V 10/764* (2022.01); *G06V 20/20* (2022.01); *A61B 2090/365* (2016.02); *A61B 2090/368* (2016.02); *G06T 2200/24* (2013.01); *H04L 67/12* (2013.01)

(58) Field of Classification Search
None
See application file for complete search history.

(56) References Cited

U.S. PATENT DOCUMENTS

| | | | |
|---|---|---|---|
| 6,493,872 B1 * | 12/2002 | Rangan | H04N 21/631 348/584 |
| 10,747,948 B1 * | 8/2020 | Petrov | H04N 21/4532 |
| 10,755,748 B2 * | 8/2020 | Madduluri | G11B 27/031 |
| 10,984,230 B2 * | 4/2021 | Wakako | G06V 10/10 |
| 2005/0069169 A1 * | 3/2005 | Zarrabizadeh | G06T 1/0028 382/232 |
| 2008/0154908 A1 * | 6/2008 | Datar | G06F 16/78 |

(Continued)

*Primary Examiner* — Martin Mushambo
(74) *Attorney, Agent, or Firm* — CALDWELL INTELLECTUAL PROPERTY LAW

(57) ABSTRACT

An offsite device for remote augmented reality communication for guided surgery configured to receive, by an offsite device, a plurality of representations of a plurality of frames and a plurality of indices, wherein the plurality of indices includes at least a first frame index and at least a second frame index, display, by the offsite device and to an offsite surgeon, a second frame of the second frame index, input, by the offsite device, an illustration from the offsite surgeon, wherein the illustration is drawn on the second frame, register, by the offsite device, the illustration to the second frame, wherein registering produces registration data, and transmit, by the offsite device, the illustration and the registration data.

19 Claims, 7 Drawing Sheets

(56) References Cited

U.S. PATENT DOCUMENTS

| | | | |
|---|---|---|---|
| 2008/0247744 A1* | 10/2008 | Une | G03B 17/24 |
| | | | 396/310 |
| 2012/0128241 A1* | 5/2012 | Jung | H04N 21/435 |
| | | | 382/165 |
| 2014/0258867 A1* | 9/2014 | Yang | G06F 3/0484 |
| | | | 715/723 |
| 2014/0270436 A1* | 9/2014 | Dascal | A61B 6/463 |
| | | | 382/130 |
| 2015/0049002 A1* | 2/2015 | Ishikawa | G06T 19/003 |
| | | | 345/8 |
| 2015/0063786 A1* | 3/2015 | Ma | G06F 3/0488 |
| | | | 386/282 |
| 2015/0138223 A1* | 5/2015 | Sorkine Hornung | H04N 9/73 |
| | | | 345/591 |
| 2016/0210411 A1* | 7/2016 | Mentis | G06F 3/04842 |
| 2017/0150117 A1* | 5/2017 | Tsirkin | H04N 13/398 |
| 2017/0257413 A1* | 9/2017 | Markan | H04L 65/403 |
| 2020/0167918 A1* | 5/2020 | Ando | A61B 6/465 |
| 2020/0273561 A1* | 8/2020 | Wolf | G16H 70/20 |
| 2020/0273575 A1* | 8/2020 | Wolf | G16H 15/00 |
| 2020/0273581 A1* | 8/2020 | Wolf | G06V 20/52 |
| 2021/0174522 A1* | 6/2021 | Govari | G06T 11/00 |

\* cited by examiner

US 11,751,972 B2

METHODS AND SYSTEMS FOR REMOTE AUGMENTED REALITY COMMUNICATION FOR GUIDED SURGERY

CROSS-REFERENCE TO RELATED APPLICATIONS

This application is a continuation of Non-provisional application Ser. No. 16/891,229 filed on Jun. 3, 2020 and entitled "METHODS AND SYSTEMS FOR REMOTE AUGMENTED REALITY COMMUNICATION FOR GUIDED SURGERY," the entirety of which is incorporated herein by reference.

FIELD OF THE INVENTION

The present invention generally relates to the field of image analysis and transformation. In particular, the present invention is directed to methods and systems for an offsite device for remote augmented reality communication for guided surgery.

BACKGROUND

Use of transformed images in augmented reality and other guidance systems as an aid to surgical demonstration is as yet a nascent technology, but its potential utility is becoming increasingly clear. Existing solutions, however, lack robustness necessary for use in many circumstances where they might be especially invaluable.

SUMMARY OF THE DISCLOSURE

In an aspect a method of an offsite device for remote augmented reality communication for guided surgery, wherein the method includes receiving, by an offsite device, a plurality of representations of a plurality of frames and a plurality of indices, wherein the plurality of indices includes at least a first frame index and at least a second frame index. The method further includes displaying, by the offsite device and to an offsite surgeon, a second frame of the second frame index, inputting, by the offsite device, an illustration from the offsite surgeon, wherein the illustration is drawn on the second frame, registering, by the offsite device, the illustration to the second frame, wherein registering produces registration data, and transmitting, by the offsite device, the illustration and the registration data.

In another aspect, an offsite device for remote guided surgery is configured to receive, by an augmented reality device, a plurality of representations of a plurality of frames and a plurality of indices, wherein the plurality of indices includes at least a first frame index and at least a second frame index, display, by the offsite device and to an offsite surgeon, a second frame of the second frame index, input, by the offsite device, an illustration from the offsite surgeon, wherein the illustration is drawn on the second frame, register, by the offsite device, the illustration to the second frame, wherein registering produces registration data, and transmit, by the offsite device, the illustration and the registration data.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

Embodiments disclosed herein use timing and motion detection protocols to synchronize image analysis and modification of devices interacting in remote surgical guidance. Such synchronization may enable remote devices at distances sufficient to cause substantial communication lag, at least relative to clock speeds, to interact effectively, ensuring faithful image reconstruction. Embodiments may use redundancy, error-detection and correction, and artificial intelligence protocols to enhance robustness to error introduction through noise, low lighting, radiation, temperature fluctuation, unpredictable motion and/or acceleration in a theater of operation, or the like.

Figure 1:
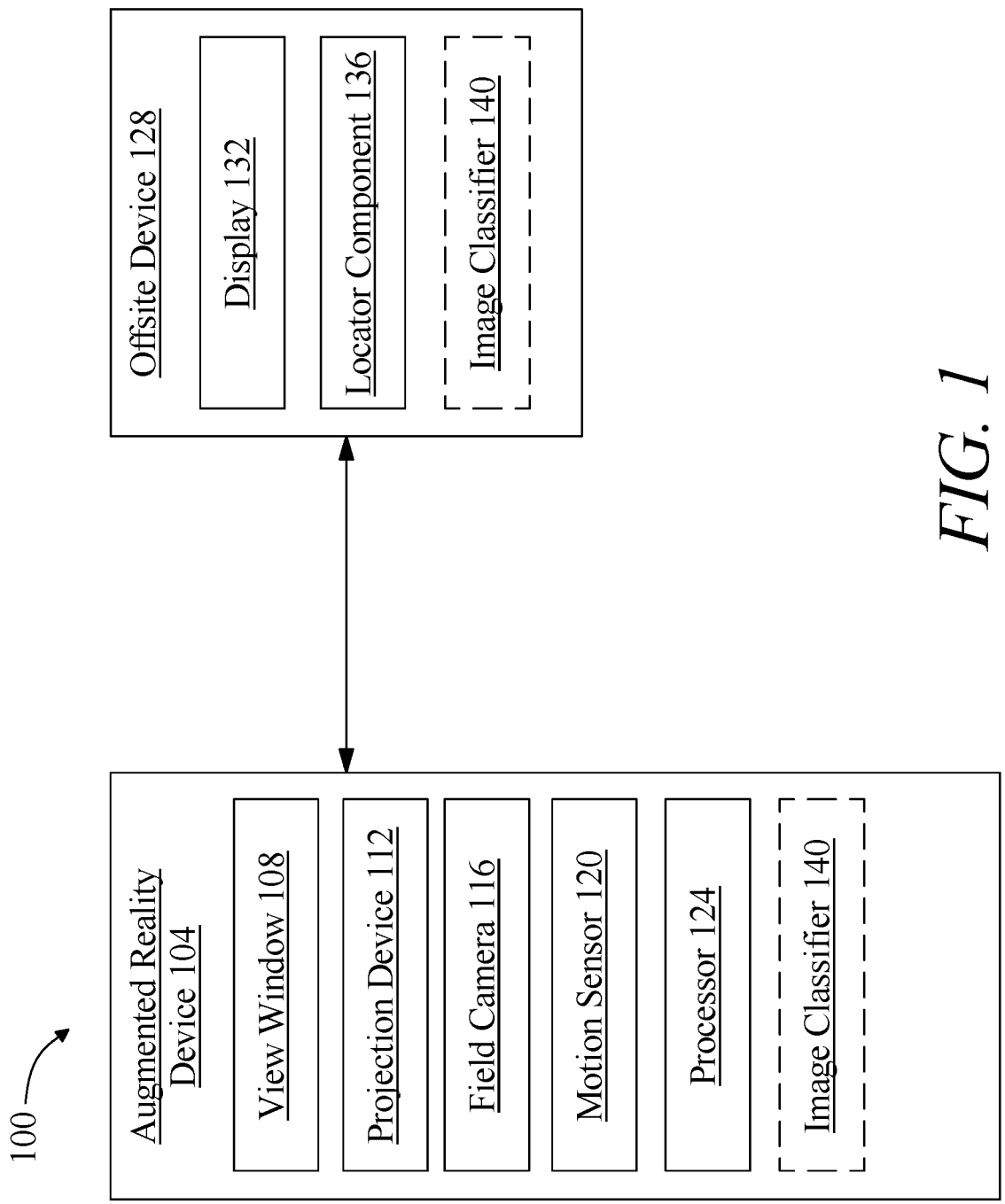
FIG. 1 is a block diagram illustrating system for remote augmented reality communication for guided surgery.

Referring now to FIG. 1, an exemplary embodiment of a system 100 for remote augmented reality communication for guided surgery is illustrated. System may include an augmented reality device 104. An "augmented reality" device, as used in this disclosure, is a device that permits a user to view a typical field of vision of the user and superimposes virtual images on the field of vision. Augmented reality device 104 may include a view window 108, defined for the purposes of this disclosure as a portion of the augmented reality device 104 that admits a view of field of vision; view window 108 may include a transparent window, such as a transparent portion of goggles such as lenses or the like. Alternatively, view window 108 may include a screen that display 132s field of vision to user. Augmented reality device 104 may include a projection device 112, defined as a device that inserts images into field of vision. Where view window 108 is a screen, projection device 112 may include a software and/or hardware component that adds inserted images into a display 132 signal to be rendered on the display 132. Projection device 112 and/or view window 108 may make use of reflective waveguides, diffractive waveguides, or the like to transmit, project, and/or display 132 images. For instance, and without limitation, projection device 112 and/or display 132 may project images through and/or reflect images off an eyeglass-like structure and/or lens piece, where either both field of vision and images from projection device 112 may be so display 132ed, or the former may be permitted to pass through a transparent surface. Projection device 112 and/or view window 108 may be incorporated in a contact lens or eye tap device, which may introduce images into light entering an eye to cause display 132 of such images. Projection device 112 and/or view window 108 may display 132 some images using a virtual retina display 132 (VRD), which may display 132 an image directly on a retina of onsite surgeon.

Still referring to FIG. 1, augmented reality device 104 may be implemented in any suitable way, including without limitation incorporation of or in a head mounted display 132, a head-up display 132, a display 132 incorporated in eyeglasses, googles, headsets, helmet display 132 systems, or the like, a display 132 incorporated in contact lenses, an eye tap display 132 system including without limitation a laser eye tap device, VRD, or the like. Augmented reality device may alternatively or additionally be implemented using a projector, which may display images received from offsite surgeon, as described in further detail below, onto an operation locus as described in further detail below. Persons skilled in the art, upon reviewing the entirety of this disclosure, will be aware of various optical projection and/or display 132 technologies that may be incorporated in augmented reality device 104 consistently with this disclosure.

Further referring to FIG. 1, view window 108, projection device 112, and/or other display 132 devices incorporated in augmented reality device 104 may implement a stereoscopic display 132. A "stereoscopic display 132," as used in this disclosure, is a display 132 that simulates a user experience of viewing a three-dimensional space and/or object, for instance by simulating and/or replicating different perspectives of a user's two eyes; this is in contrast to a two-dimensional image, in which images presented to each eye are substantially identical, such as may occur when viewing a flat screen display 132. Stereoscopic display 132 may display 132 two flat images having different perspectives, each to only one eye, which may simulate the appearance of an object or space as seen from the perspective of that eye. Alternatively or additionally, stereoscopic display 132 may include a three-dimensional display 132 such as a holographic display 132 or the like. Persons skilled in the art, upon reviewing the entirety of this disclosure, will be aware of various alternative or additional types of stereoscopic display 132 that may be employed in augmented reality device 104.

Continuing to refer to FIG. 1, augmented reality device 104 may include a field camera 116. A "field camera 116," as used in this disclosure, is an optical device, or combination of optical devices, configured to capture field of vision as an electrical signal, to form a digital image. Field camera 116 may include a single camera and/or two or more cameras used to capture field of vision; for instance, and without limitation, the two or more cameras may capture two or more perspectives for use in stereoscopic and/or three-dimensional display 132, as described above. Field camera 116 may capture a feed including a plurality of frames, such as without limitation a video feed.

Still referring to FIG. 1, augmented reality device 104 may include at least a motion sensor 120. At least a motion sensor 120 may include, without limitation, a microelectromechanical system (MEMS) sensor. At least a motion sensor 120 may include, without limitation, an inertial measurement unit (IMU). At least a motion sensor 120 may include one or more accelerometers; one or more accelerometers may include a plurality of accelerometers, such as three or more accelerometers positioned to span three dimensions of possible acceleration, so that any direction and magnitude of acceleration in three dimensions may be detected and measured in three dimensions. At least a motion sensor 120 may include one or more gyroscopes; one or more gyroscopes may include a plurality of gyroscopes, such as three or more gyroscopes positioned to span three dimensions of possible acceleration, so that any direction and magnitude of change in angular position in three dimensions may be detected and measured in three dimensions. At least a motion sensor 120 may include, without limitation magnetic sensors such as Hall effect sensors, compasses such as solid-state compasses, or the like. Persons skilled in the art, upon reviewing the entirety of this disclosure, will be aware of various components and/or devices that may be used as at least a motion sensor 120 consistently with this disclosure.

Augmented reality device 104 may include a processor 124. Processor 124 may include and/or be included in any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 124 may include and/or be included in a single computing device operating independently, or may include two or more computing device operating in concert, in parallel, sequentially or the like; two or more computing devices may be included together in a single computing device or in two or more computing devices. Processor 124 may interface or communicate with one or more additional devices as described below in further detail via a network interface device. Network interface device may be utilized for connecting processor 124 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 124 may include but is not limited to, for example, a computing device or cluster of computing devices in a first location and a second computing device or cluster of computing devices in a second location. Processor 124 may include and/or be included in one or more computing devices dedicated to data storage, security, distribution of traffic for load balancing, and the like. Processor 124 may distribute one or more computing tasks as described below across a plurality of computing devices of computing device, which may operate in parallel, in series, redundantly, or in any other manner used for distribution of tasks or memory between computing devices. Processor 124 may be implemented using a "shared nothing" architecture in which data is cached at the worker, in an embodiment, this may enable scalability of system 100 and/or computing device.

Still referring to FIG. 1, processor 124 may include a device and/or component incorporated in and/or attached to augmented reality device 104. For instance, processor 124 may include a microcontroller, system on chip, FPGA, or other compact hardware element that is incorporated in and/or attached to augmented reality device 104. Alternatively or additionally, processor 124 may include a device communicating with augmented reality device 104 via a wireless and/or wired connection. In an embodiment, processor 124 may include a device incorporated in augmented reality device 104 and a device communicating therewith via wired and/or wireless connection.

Processor 124 may be designed and/or configured to perform any method, method step, or sequence of method steps in any embodiment described in this disclosure, in any order and with any degree of repetition. For instance, processor 124 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 124 may perform any step or sequence of steps as described in this disclosure in parallel, such as simultaneously and/or substantially simultaneously performing a step two or more times using two or more parallel threads, processor 124 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Figure 2:
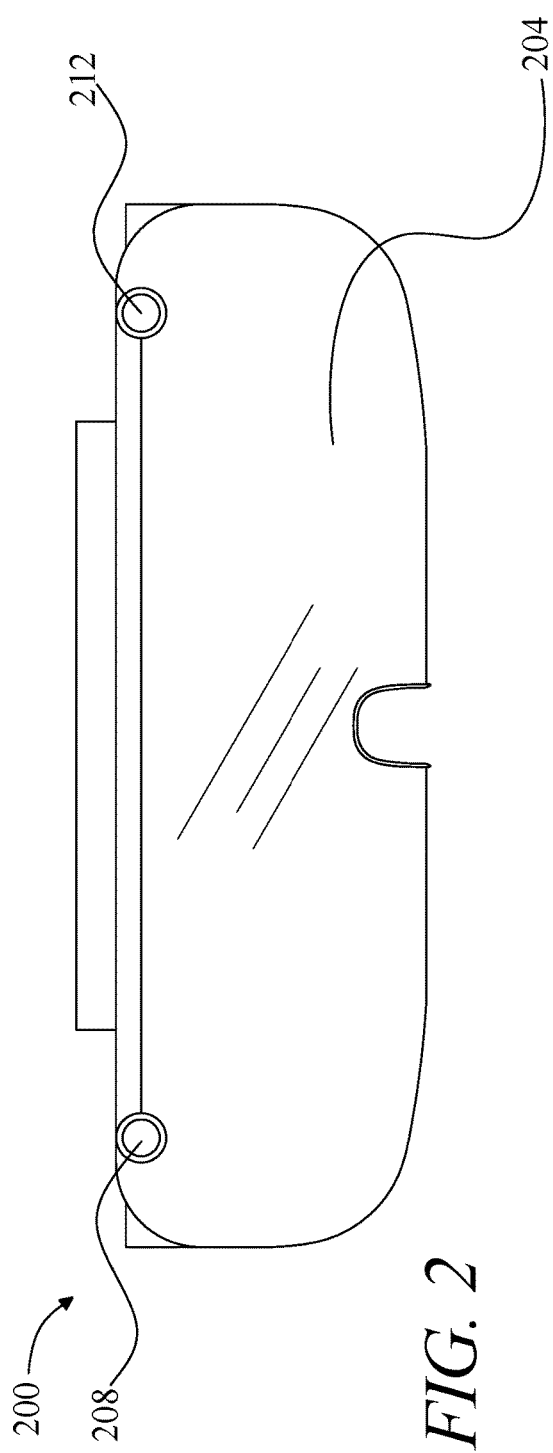
FIG. 2 is a schematic diagram of an embodiment of an augmented reality device.

Referring now to FIG. 2 an exemplary embodiment of a front view 200 of an augmented reality device is depicted. As a non-limiting example, augmented reality device 104 may take a form of a pair of goggles or eyewear, and/or may be incorporated in a headset or the like. Augmented reality device may include a lens 204, through which onsite surgeon may view field of vision; lens 204 may function as view window 108 in an embodiment. Augmented reality device 108 may include a right camera 208 and/or a left camera 212, which may capture stereoscopic images and video as described above.

Figure 3:
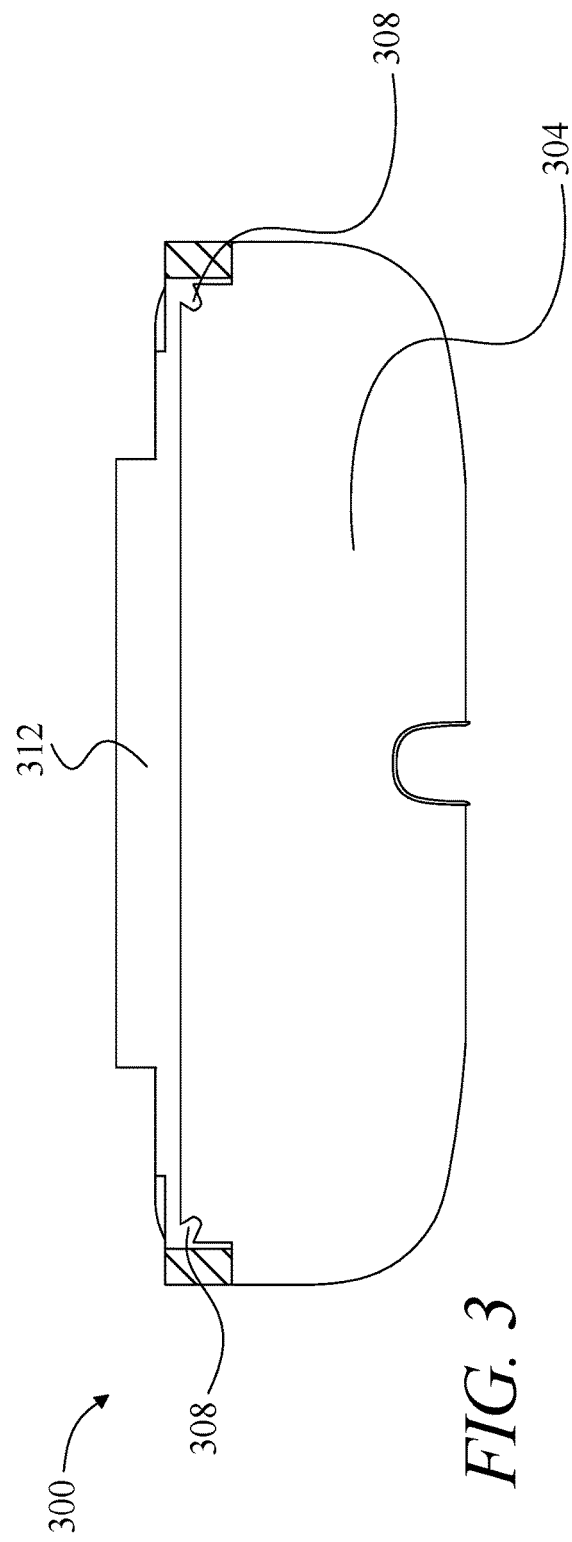
FIG. 3 is a schematic diagram of an embodiment of an augmented reality device.

Referring now to FIG. 3, an exemplary embodiment of a rear view 300 of an augmented reality device is illustrated. Device 108 may include a display 304, which may function as view window 108 and/or projection device 112. Alternatively or additionally, one or more projectors 308 may project images on display. A component housing 312 may include circuitry, a power source such as a battery and/or a port for an external power source connection, one or more components of processor 124, or the like.

Referring again to FIG. 1, system may include an offsite device 128. Offsite device 128 may include any processor and/or computing device containing any processor suitable for use in and/or with augmented reality device 104 as described above. Offset device may include any component and/or element suitable for use with augmented reality headset. Offset device may be designed and/or configured to perform any method, method step, or sequence of method steps in any embodiment described in this disclosure, in any order and with any degree of repetition. For instance, offsite device 128 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Offsite device 128 may perform any step or sequence of steps as described in this disclosure in parallel, such as simultaneously and/or substantially simultaneously performing a step two or more times using two or more parallel threads, offsite device 128 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, offsite device 128 may include a display 132. Display 132 may include, without limitation any display 132 as described in this disclosure, including without limitation any display 132 usable with augmented reality headset. Offsite device 128 may include a locator component 136. A "locator component 136," as used in this disclosure, is a device and/or component that a user can use to point a cursor at a point on a display 132 and/or to draw on an image depicted in the display 132. A locator component 136 may include without limitation a wired or wireless mouse, a touchpad, a touchscreen, a game controller, or the like. A locator component 136 may include a motion-capture device, such as without limitation a device that tracks motion of offsite surgeon's hands optically and/or using a sensor of motion, which may be implemented in any way suitable for implementation of a motion sensor 120 as described above. Persons skilled in the art, upon reviewing the entirety of this disclosure, will be aware of various ways in which a locator device may be implemented consistently with this disclosure.

Still referring to FIG. 1, augmented reality device 104 and/or offsite device 128 may be configured to generate and/or classify images using an image classifier 140. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, kernel estimation, learning vector quantization, and/or neural network-based classifiers.

Still referring to FIG. 1, image classifier 140 may be generated, as a non-limiting example, using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)÷P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, image classifier 140 may be generated using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, augmented reality device 104 and/or offsite device 128 may be configured to train image classifier 140 using any classification algorithm described above operating on training data. "Training data," as used herein, is data containing correlations that a machine-learning process, such as a classifier, may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and further referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. Training data used to train image classifier 140 may include a plurality of entries, each including attributes of an image such as a portion of a frame of a plurality of frames, and/or a shape detected therein, which may be used to classify the image to other images in training data.

Figure 4:
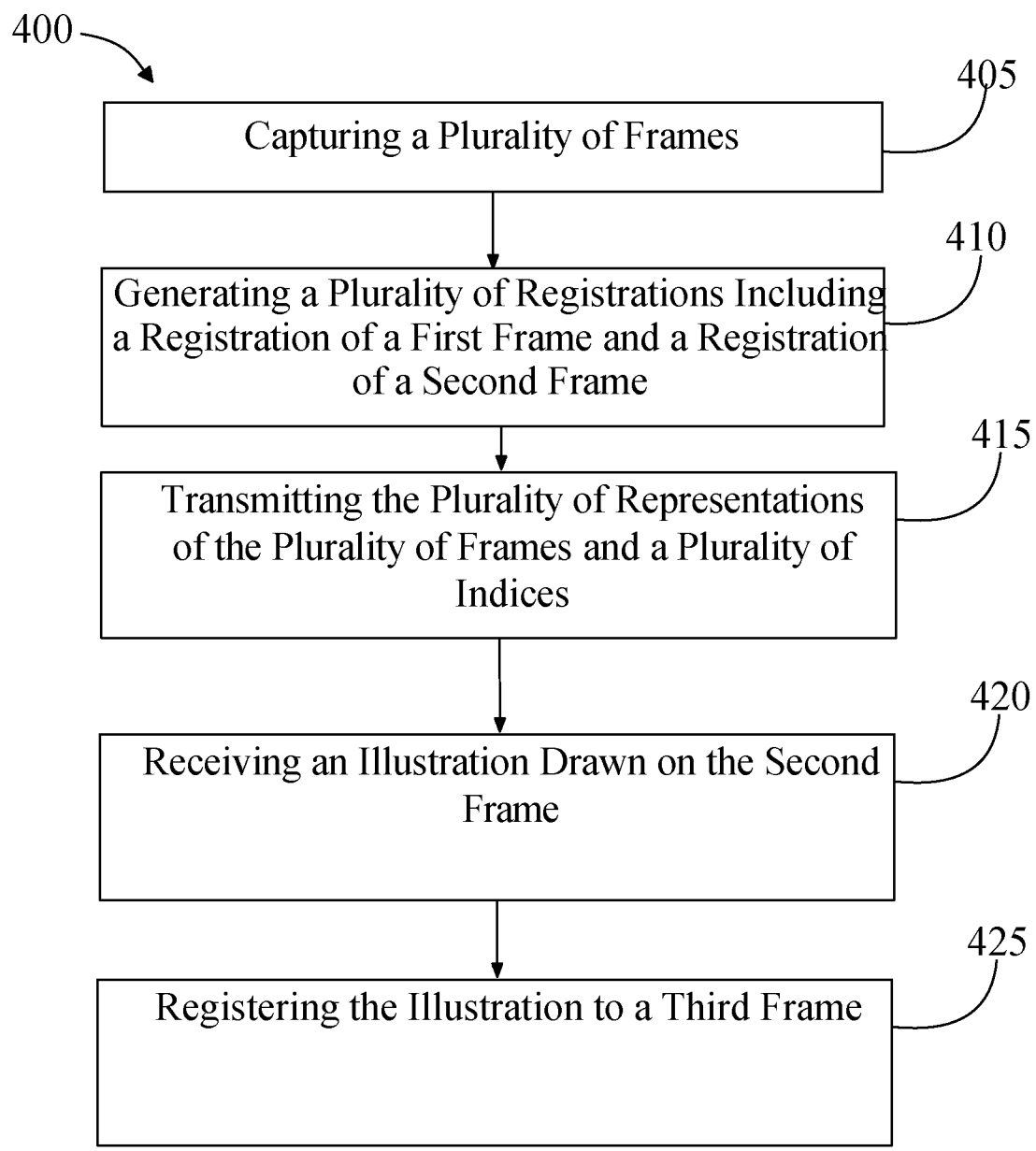
FIG. 4 is a flow diagram of an embodiment of a method for remote augmented reality communication for guided surgery.

Referring now to FIG. 4, an exemplary embodiment of a method 400 of remote augmented reality communication for guided surgery is illustrated. At step 405, an augmented reality device 104 capture a feed including a plurality of frames, wherein each frame includes an image of a field of vision of an onsite surgeon. Field of vision may include a field of vision in front of onsite surgeon and may include one or more elements of an operating theater in which onsite surgeon is operating. Each frame may have a coordinate system for location of pixels on frame, as determined, for instance, by setting an origin point on frame, such as a vertex where frame is rectangular, and counting pixels horizontally and vertically from the origin point.

Continuing to refer to FIG. 4, "onsite surgeon" may include a person qualified as a surgeon, a medical professional, and/or any person who is performing surgery and/or assisting in performance thereof, for instance as necessitated by an emergent situation. Onsite surgeon may perform one or more medical operations on a patient in a theater, where a "theater" may include any operating room, makeshift or field operating room, medical tent, a vehicle such as an ambulance, rescue wagon, rescue or medical evacuation helicopter and/or drone, or the like. In an embodiment, onsite surgeon may be called upon to perform one or more medical operations under circumstances that limit resources, personnel, facilities, or the like. For instance, onsite surgeon may be deployed on a military mission, in a research station in a remote location such as Nunavut and/or *Antarctica*, or on a space flight location and/or trip such as a space capsule, space plane, space station, orbital facility, lunar base, and/or mission to the Moon or other planets, where transportation of goods and/or persons may be difficult and/or impossible due to seasonal weather, or the like. Alternatively or additionally, temporary circumstances such as a natural disaster may cause the limitations of personnel, supplies, and/or facilities; for instance, an earthquake, volcano, a storm, flooding, and/or wildfires may cut off transportation, or power, incapacitate personnel, and/or damage facilities, requiring some compromise. This may require, for instance, that a general practice doctor perform trauma surgery, that a trauma surgeon extract a biopsy sample or perform an appendectomy, or that a nurse practitioner or person with limited medical training perform an operation they have not learned to perform. Alternatively or additionally, circumstances as described above may require onsite surgeon to use a limited set of equipment, to perform field sterilization, to use an unfamiliar piece of equipment, and/or to perform medical operations without accustomed oversight and/or support staff.

Still referring to FIG. 4, circumstances as described above may introduce one or more obstacles to effective communication and processing. For instance, a distance to a remote location such as a location on or on a space flight location and/or trip such as a space capsule, space plane, space station, orbital facility, lunar base, and/or mission to the Moon or other planets may introduce communication lag, presenting synchronization challenges; offsite surgeon may be looking at images some seconds after they have been captured and transmitted, and onsite surgeon, upon receiving guidance from offsite surgeon, will be receiving such guidance with regard to an image that was transmitted several seconds ago. In addition, circumstances described above may cause signal degradation and/or introduce errors in circuitry; for instance, and without limitation, radiation and/or high-speed particles in space environments may cause one or more bits to flip, which may change one or more pixel coordinates to be misplaced, one or more state machines to enter incorrect and/or illegal states, or the like. Similarly, processes may be interrupted as a result of circumstances that decrease mean time between failures, increase static computation time of combinational circuits, or otherwise halt or produce inaccurate results that may cause further data and/or communication inaccuracies. Noise introduction may also render one or more bits unreadable or introduce errors. Each of these problems may be exacerbated by greater distances of communication, owing to a greater possibility of noise exposure and a requirement for more devices to relay signals, which may increase probability of failure or erroneous transmission by any device in the chain. Furthermore, circumstances as described above may cause periodic interruptions or failures, particularly of video data.

Further referring to FIG. 4, medical operation may include any medical, life-saving, and/or other treatment procedure, such as without limitation any surgical operation, biopsy extraction, endoscopy and/or other probing and/or inspection technique, intubation, catheterization, insertion of intravenous lines, extraction of samples of blood, lymph, cerebrospinal fluid, amniotic fluid, vitreous humor, tissue samples such as skin samples mucous membrane samples and/or one or more samples of microbiota, injections of vaccines and/or mediations, blood, plasma, and/or fluid transfusions, extraction of parasites such as filarial worms, ascarid worms, fly larvae, ticks, or the like, excision of tissue compromised by gangrene, leishmaniasis, cell death due to envenomation, frostbite, burns, lack of oxygen due to compartment syndrome, extended periods of pressure and/or tourniquet application, or the like, amputation, bandaging and/or suturing procedures, emergency procedures such as tracheotomy, administration of epinephrine, and/interventions to alleviate and/or interrupt cardiac fibrillation, seizures and/or stroke, medical paralysis, placement of electrodes or other externally or internally mounted devices used in diagnostic procedures such as electrocardiograms, electroencephalograms, or the like, radiological procedures such as ultrasound, x-ray, computer assisted tomography, magnetic resonance imaging, optical scanning procedures, and/or positron emission tomography, craniotomy, or the like. Procedures to be performed may include, without limitation, abscess incision and/or drainage, including superficial abscess incision and/or drainage, debridement, foreign body removal, hemorrhoid banding/excision, hernia repair (open), laceration repair, NGT insertion, skin graft, cricothyroidotomy, fasciotomies, needle decompression, tourniquet placement, traction splinting, tube thoracostomy, intubation, local and/or regional pain blocks, cerumen removal, peritonsillar abscess drainage, tympanostomy tube placement, bladder catheterization, GU lesion excision, amputation, fracture and/or dislocation treatments such as incision/drainage (MSK) and/or splinting/casting, ultrasound-guided procedures such as arterial line, central line, diverticular and/or appendicular (intraabdominal) abscess drainage, limb blocks, and/or percutaneous cholecystostomy tube, and/or scope-guided procedures such as upper endoscopy (EGD) and/or banding, flexible sigmoidoscopy, cyst-gastrostomy, tracheostomy, bronchoscopy, cystoscopy and/or ureteral stenting, and/or any other procedure and/or combination of procedures that may occur to persons skilled in the art.

At step 410, and continuing to refer to FIG. 4, augmented reality device 104 generates a plurality of registrations matching each frame of the plurality of frames to a field coordinate system. A "field coordinate system," as used herein is a coordinate system of the field of view, such as a Cartesian coordinate system a polar coordinate system, or the like; field coordinate system does not depend on a head position of onsite surgeon and/or a position of augmented reality device 104. In other words, a position of an object within the field coordinate system is static unless the object is moved. Field coordinate system may include a three-dimensional coordinate system. An origin point of field coordinate system may be selected, without limitation, for convenience of calculation, such as selection of a pixel on a frame, such as a first frame as described below which may include without limitation an origin point on a coordinate system of first frame.

Still referring to FIG. 4, generating plurality of registrations includes defining a first registration of a first frame to the field coordinate system. "Registration" of a frame to a coordinate system, as used in this disclosure, means identifying a location within the coordinate system of each pixel of the frame, either by directly identifying the location of each pixel, and/or by identifying a location of a sufficient number of pixels, such as corner pixels or the like, of the frame to make mathematical determination of location of all other pixels mathematically possible; registration may include identifying coordinates of some excess number of pixels to the minimal number needed to identifying position within the coordinate system, such as identification of one pixel more, twice as many pixels, or ten times as many pixels, where excess pixels may be used to perform error detection and/or correction as described in further detail below. Registration of a frame to field coordinate system may be characterized as a map associating each pixel of a frame, and/or coordinates thereof in a frame coordinate system, to a pixel of field coordinate system. Such mapping may result in a two-dimensional projection of corresponding three-dimensional coordinates on one or more two-dimensional images. First frame may be selected at startup of augmented reality device 104, upon entry of a user command indicating that user is ready to begin process, that user is facing operating table, and/or that an operating locus is in frame; first frame may be selected as a frame generated when such command is received. Alternatively or additionally, defining the first registration may include detecting an operation locus, determining that the operation locus is centrally located in the first frame, and registering the first frame to the field coordinate system. First frame may include two frames where two frames are captured for stereoscopic images; in this case each such frame may be separately registered, and corresponding subsequent frames may be registered with regard to corresponding original first frame. In the description that follows, it should be assumed that each process described may be performed in parallel on two families or streams of frames forming a stereoscopic image.

Further referring to FIG. 4, detecting operation locus may include detecting a shape using an image recognition algorithm identifying the detected shape as the operation locus. Image recognition algorithm may include an edge-detection algorithm, which may detect one or more shapes defined by edges. An "edge detection algorithm," as used in this disclosure, includes a mathematical method that identifies points in a digital image at which the image brightness changes sharply and/or has discontinuities. In an embodiment, such points may be organized into straight and/or curved line segments, which may be referred to as "edges." Edge detection may be performed using any suitable edge detection algorithm, including without limitation Canny edge detection, Sobel operator edge detection, Prewitt operator edge detection, Laplacian operator edge detection, and/or Differential edge detection. Edge detection may include phase congruency-based edge detection, which finds all locations of an image where all sinusoids in the frequency domain, for instance as generated using a Fourier decomposition, may have matching phases which may indicate a location of an edge. Edge detection may be used to detect a substantially quadrilateral shape formed by surgical drapes, indicating a window about an incision site; in an embodiment, edge detection algorithm may be used to find closed figures formed by edges, such a window in surgical drapes about an operating site. A user such as onsite surgeon and/or offsite surgeon may be provided with a plurality of such closed figures, and/or other figures identified using edge detection process; augmented reality device 104 may receive an indication from at least one of the onsite surgeon and the offsite surgeon that the detected shape is the operation locus.

Alternatively or additionally, and still referring to FIG. 4, identifying detected shape as an operation locus may include classifying the detected shape to a label identifying operation loci using an image classifier 140 as described above; image classifier 140 may be trained using a plurality of images of operation loci. Image classifier 140 may be configured to determine which of a plurality of edge-detected shapes is closest to an attribute set of an operation locus as determined by training using training data and selecting the determined shape as an operation locus. Where operation locus is automatically selected, selection may be display 132*ed* to onsite surgeon, offsite surgeon and/or another user for verification; a positive verification may cause augmented reality device 104 and/or offset surgeon device to use determined shape as operation locus, while a negative response may cause augmented reality device 104 and/or offset surgeon device to select a second-best match and repeat the above steps. Alternatively, identification of operating locus may be performed without using computer vision and/or classification; for instance, identifying the operation locus further comprises receiving, from at least one of the onsite surgeon and the offsite surgeon, an identification of the operation locus in at least a frame. User identification may include a tap on or near a geometric center of operation locus, and/or a drawing of a boundary about operation locus. Where offsite surgeon provides identification, this may be performed similarly to any offsite surgeon inputs as described in further detail below. Operation locus, once defined, may be identified using a set of vertices and/or other pixels of operation locus in known positions relative to field coordinate system.

Still referring to FIG. 4, offsite device 128 may select first frame from a plurality of potential frames, on which to pause, based on image quality as described above, including a frame maximizing image quality generally and/or maximizing image quality at operation locus. Selection according to image quality may, for instance, minimize error and/or maximize accuracy and/or robustness to interference by any circumstantial factors as described above using without limitation any process for error prevention, detection, and/or correction as described in this disclosure, for instance by furnishing a greater ability to perform image recognition and resulting cross-checks. As a non-limiting example, image quality may vary with a flickering and/or intermittent light source, or as caused by intermittent interruptions, for instance as a result of one or more circumstances as described above, such that image selection based on image quality may capture a relatively low-noise, focused image, when an intermittent light source is high enough to provide better contrast and detail. Selection based on image quality may be combined with selection based on central location of operation locus. In an embodiment, where image quality falls below a threshold as described above, an indication may display to onsite surgeon and/or offsite surgeon that image quality is low, permitting, for instance, onsite surgeon to seek more lighting, check network connections, or the like.

With continued reference to FIG. 4, registration of plurality of frames may include detecting a motion of augmented reality device 104 from the first frame to a second frame. Motion may be represented, without limitation as a vector; for instance x, y, and z components of motion may be detected using any process described in this disclosure for detection and/or determination of motion; each component may be formed by aggregation of a components detected from a series of motions between first frame and second frame. Motion detection may be synchronized to frame rate, for instance as coordinated by a central clock and/or one or more peripheral device clocks and/or counters. Although motion has been described here as represented in vector form, motion may be represented with any alternative or additional data structure, including any mathematical equivalent to a motion vector. Detecting the motion of the augmented reality device 104 from the first frame to the second frame may include detection of the motion using motion sensor 120. Detection may alternatively or additionally include detecting motion of an object in field of vision relative to augmented reality device 104; object may include operation site, as defined above, or any other object as detected, without limitation, using image classifier 140 as described above. In an embodiment, the above two methods may be combined; for instance, detection of motion may include detection of the motion of a motion sensor 120 incorporated in augmented reality device 104, detection of motion of an object in field of vision, and combination of the detected motion of the motion sensor 120 with the detected motion of the object in the field of vision. Vectors detected in two or more processes may be combined by averaging together or otherwise aggregating components to produce a composite vector, unless image quality falls below a threshold level as described below, in which case only motion sensor 120 detection may be used, where threshold may be stored as a configured numerical quantity.

In an embodiment, and continuing to refer to FIG. 4, detection of motion using detected motion of objects in field of vision may be contingent on image quality; for instance, in low-light conditions and/or under other circumstances in which picture quality makes image recognition problematic, augmented reality device 104 may avoid use of image detection and/or classification to detect motion. As a non-limiting example, augmented reality device 104 may detect image quality in the plurality of frames, comparing the image quality to a preconfigured threshold, stored for instance as a numerical quantity, and using the motion of an object in field of vision only if the image quality satisfies the preconfigured threshold. "Image quality," as used in this disclosure may include without limitation, a score representing contrast level, a degree of noise, and/or a degree of blurriness, and/or an aggregation and/or addition of two or more such scores. Contrast, blurriness, and some kinds of noise may be detected using a fast Fourier transform (FFT) or other degree of variation detection, where an FFT may show a predominance of lower frequency across the signal for images with degraded contrast, increased blurriness, and/or increased noise. Alternatively or additionally, a classifier of like photographic images may be used to detect higher and lower quality images, for instance and without limitation as taught by user entries identifying image quality; classifier may be trained and/or implemented, without limitation, as described above for training and/or implementation of image classifier 140.

Further referring to FIG. 4, an object and/or shape identified using image classifier 140, such as operation locus, a window in surgical dressings, and/or an anatomical feature of interest, may be assigned an object identifier by augmented reality device 104. Computing device may further record one or more sets of coordinates describing location of an identified object; coordinates may include a set of coordinates of an approximate geometric center of object, coordinates of a plurality of vertices of polygonal approximations of surface features, or the like. Any such coordinates and/or object identifier may be transmitted to offsite device 128 and/or augmented reality device 104 by augmented reality device 104 and/or offsite device 128, respectively.

Still referring to FIG. 1, augmented reality device 104 generates an affine motion transformation as a function of the detected motion and calculates a second registration of the second frame to the field coordinate system. An "affine motion transformation," as used in this disclosure, may include any mathematical description usable to describe an affine motion of pixels in a display 132 relative to field coordinate system, where "affine motion" is a motion within a space, such as three-dimensional space, which preserves ratios of lengths of parallel line segments. For instance, and without limitation, affine transformations in three dimensions may be represented by 4×4 matrices. For instance, a translation by a vector [x, y, z] in x, y, and z components of motion according to a Cartesian coordinate system may be represented by the four-by-four matrix:

$$\begin{bmatrix} 1 & 0 & 0 & x \\ 0 & 1 & 0 & y \\ 0 & 0 & 1 & z \\ 0 & 0 & 0 & 1 \end{bmatrix}$$

Rotations in three dimensions can be represented generally by 4×4 matrices as well. For instance, rotations may be represented by multiplying each coordinate set by a matrix computed using Euler angles $\psi$, $\theta$, and $\phi$, representing rotations confined to the yz plane, the zx plane, and the xy plane; these angles may be referred to as roll, yaw, and pitch, respectively. Generally, rotations may be represented by a matrix M, computed as follows:

$$M = \begin{bmatrix} 1 & 0 & 0 \\ 0 & \cos(\psi) & -\sin(\psi) \\ 0 & \sin(\psi) & \cos(\psi) \end{bmatrix} \begin{bmatrix} \cos(\theta) & 0 & \sin(\theta) \\ 0 & 1 & 0 \\ -\sin(\theta) & 0 & \cos(\theta) \end{bmatrix} \begin{bmatrix} \cos(\phi) & -\sin(\phi) & 0 \\ \sin(\phi) & \cos(\phi) & 0 \\ 0 & 0 & 1 \end{bmatrix}$$

Affine transformations may be represented, without limitation, using any alternative or additional mathematical representations and/or processes. Calculation and derivation of linear transformations may be performed, without limitation, using an FPGA, ASIC, or other dedicated hardware module designed to perform rapid arithmetic; trigonometric functions may, as a non-limiting example, be implemented as lookup tables stored, for instance, in read-only memory (ROM) or the like. Alternatively or additionally, one or more such storage and/or processes may be performed by microprocessor 124s, microcontrollers, or the like, for instance in assembly language or in higher-order languages. Lookup tables, transformation computations, and/or storage of vector and/or matrix values may be performed redundantly, for use in error detection and/or correction, as described in further detail below. Augmented reality device 104 may repeat the above-described process to register a plurality of frames and/or each frame of plurality of frames based on registration of first frame.

In an embodiment, and where image quality is sufficiently high according without limitation, to threshold comparisons as described above, registration of first frame to field coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras for stereoscopic display 132, as described above, image recognition and/or edge detection software may be used to detect a pair of stereoscopic views of images of an object, such as operation locus; two stereoscopic views may be compared to derive z-axis values of points on object permitting, for instance, derivation of further z-axis points within and/or around the object using interpolation. This may be repeated with multiple objects in field of view, including without limitation anatomical features of interests identified by object classifier and/or indicated by onsite surgeon and/or offsite surgeon. In an embodiment, x and y axes may be chosen to span a plane common to two cameras used for stereoscopic image capturing and/or an xy plane of a first frame; a result, x and y translational components and $\phi$ may be pre-populated in translational and rotational matrices, as described above, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that an operation locus is substantially orthogonal to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. Of note, where two camera views and x-y coordinates chosen for a common plane are used as described above, only z coordinates may be derived in this manner. Z-coordinates, or in the case of use of successive frames from a single camera, may be further iteratively compared to objects detected in additional frames to further minimize error functions.

Figure 5:
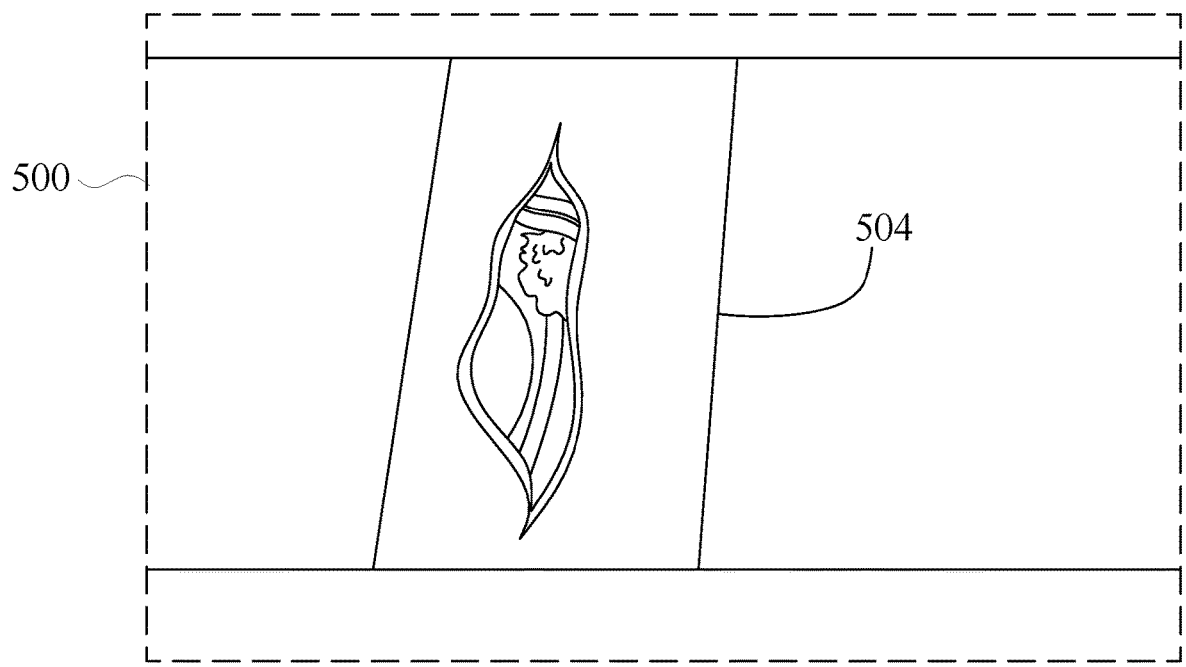
FIG. 5 is a schematic diagram of an embodiment of a first frame.
Figure 6:
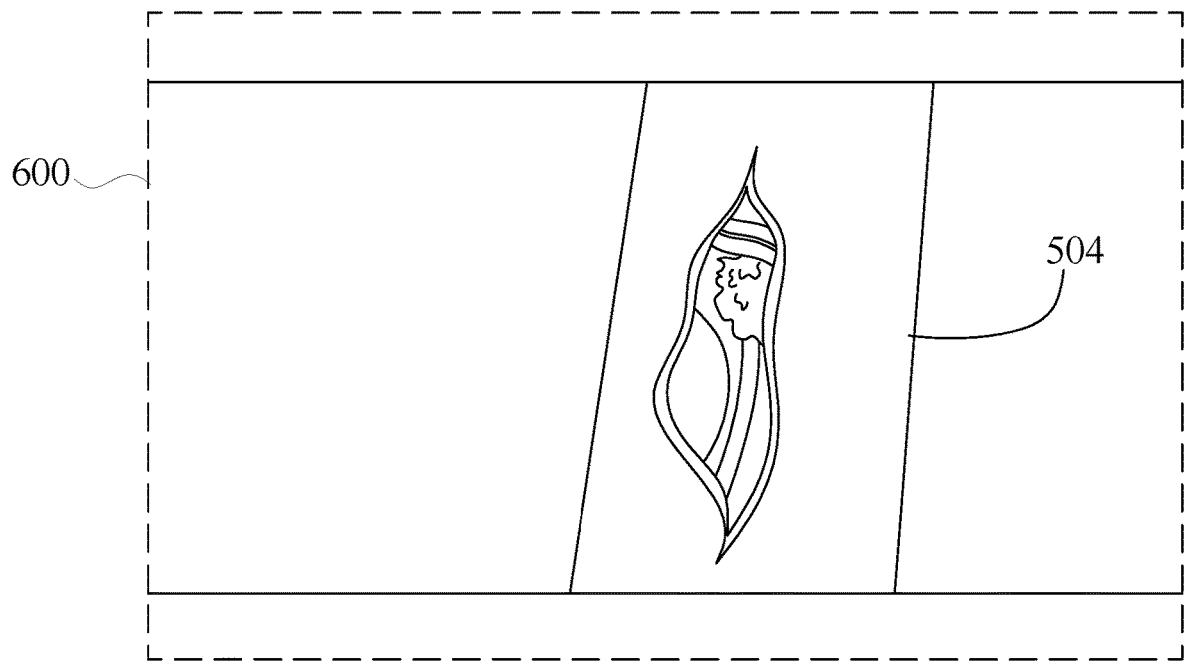
FIG. 6 is a schematic diagram of an embodiment of a second frame.

Referring now to FIG. 5, an exemplary embodiment of first frame 500 with operation locus 504 is depicted. FIG. 6 depicts a second frame 600 which has been translated to the left relative to field coordinate system, so that operation locus 504 has shifted to the right.

Returning to FIG. 4, at step 415, augmented reality device 104 transmits data, to an offsite device 128 operated by an offsite surgeon; data may be transmitted in a bitstream or the like. Transmission may include transmission a plurality of representations of the plurality of frames; this may be effected using any protocol for transmission of video data over bitstreams using lossy and/or lossless video compression, including without limitation transmission of residuals, reference frames, motion vectors, encoding and/or decoding modes, or the like. Persons skilled in the art, upon reviewing the entirety of this disclosure, will be aware of various processes and/or protocols according to which a plurality of frames and/or a video feed may be transmitted over a network consistently with this disclosure. Transmission may include, without limitation, transmission of a plurality of indices, each index corresponding to a frame of the plurality of frames, wherein the plurality of indices includes a first frame index identifying first frame and a second frame index identifying second frame; additional indices may identify each frame of plurality of frames. Indices may be in a sequential order such as an order in which frames were recorded. Transmitting may include transmitting the plurality of registrations; for instance, and without limitation, coefficients and/or matrix values for affine transformations may be transmitted. Transmitting may include transmitting an identification of at least a reference pixel. Transmission may include transmission of one or more object identifiers and/or coordinates of objects recognized using edge detection and/or image classification as described above.

Still referring to FIG. 4, at step 420, augmented reality device 104 receives, from the offsite device 128, an illustration drawn on the second frame. Offsite device 128 may display 132 plurality of frames to offsite surgeon, using any display 132 of offsite device 128 as described above; display 132 may include display 132 as a video and/or display 132 of frames. Display may include, without limitation, display of a grid of lines superimposed on operation locus; grid may be automatically generated on a plane intersecting vertices of a window created by surgical drapes and/or vertices of a rectangular or other polygonal shape drawn around operation locus. Grid may be projected on and/or attached to operation locus in any manner suitable for association with and/or display on objects in field of view of illustrations, as described in further detail in this disclosure. In an embodiment, offsite surgeon may manually and/or verbally enter a command to pause video so offsite surgeon may draw on a single frame, and/or pause and then move backward or forward to select a view the offsite surgeon may wish to draw upon; in such cases, offsite device 128 may select a frame of a plurality of potential frames, on which to pause, based on image quality as described above, including a frame maximizing image quality generally and/or maximizing image quality at operation locus. Selection according to image quality may, for instance, minimize error and/or maximize accuracy and/or robustness to interference by any circumstantial factors as described above using without limitation any process for error prevention, detection, and/or correction as described in this disclosure, for instance by furnishing a greater ability to perform image recognition and resulting cross-checks. As a non-limiting example, image quality may vary with a flickering and/or intermittent light source, or as caused by intermittent interruptions, for instance as a result of one or more circumstances as described above, such that image selection based on image quality may capture a relatively low-noise, focused image, when an intermittent light source is high enough to provide better contrast and detail. Offsite device 128 may receive illustration from offsite surgeon using locator device as described above, which offsite surgeon may use to indicate an anatomical feature of interest, an action to be performed, or the like using telestration, insertion of arrows or other elemental forms, or otherwise drawing to instruct onsite surgeon in one or more actions to be performed during medical operation.

Continuing to view FIG. 4, where surgeon is drawing without pausing video, offsite device 128 may automatically pause upon detection of initiation of drawing. Alternatively, where motion of frames relative to field of view is relatively low, offsite device 128 may record drawing as being place on one of a plurality of frames present during drawing; detection of relative stasis as described above may be performed by comparing a degree of motion between frames, as determined by affine transformations computed and/or signaled as above, and/or using other processes such as discrete cosine transformation, to a threshold, where exceeding threshold causes offsite device 128 to pause. Geometry of a mark or other illustration the surgeon enters may be recorded on a coordinate system of a third frame, and third frame index with geometry so characterized may be transmitted to onsite device; alternatively or additionally, offsite device 128 may register third frame and/or geometry to field coordinates using affine transformation as above. In an embodiment, offsite surgeon and/or offsite device 128 may use markings to identify an object to be registered; object may be named by the surgeon, and or selected using a menu of object identifiers, or selection of a coordinate included in an object may also be recorded as selection of the object and/or its object identifier. In an embodiment, this may permit displacement of object within field coordinate system to be detected; such displacement may cause offsite device 128 and/or augmented reality device 104 to displace an illustration placed thereon correspondingly, and/or to delete illustration so as to permit further illustrations to be placed.

Figure 7:
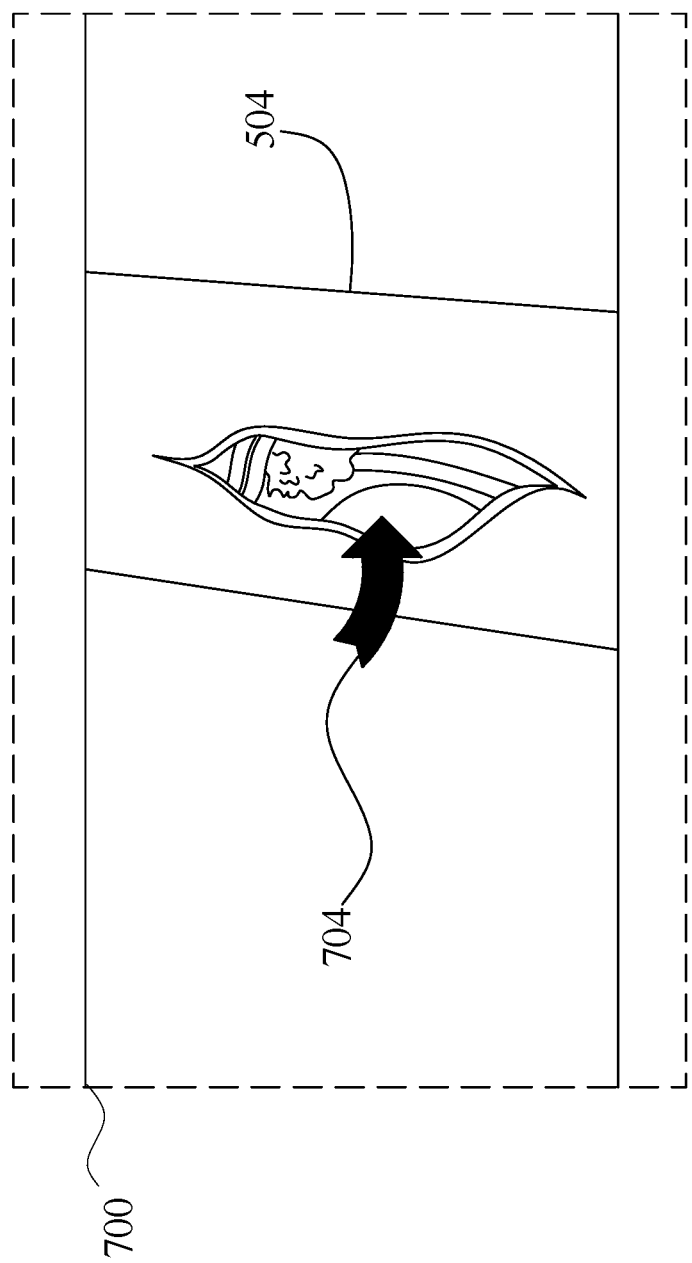
FIG. 7 is a schematic diagram of an embodiment of a third frame.

At step 425, and continuing to refer to FIG. 4, augmented reality device 104 registers illustration on a third frame of the plurality of frames. Registration includes generating a third registration of the third frame to the field coordinate system and registering the illustration on the third frame as a function of the third registration. In an embodiment, where augmented reality device 104 receives pixel locations in second frame of illustration, augmented reality device 104 may determine an affine transformation from second frame to third frame, for instance using any method described above for determining an affine transformation from first frame to second frame; augmented reality device 104 may then use affine transformation to transform pixels of illustration on second frame to pixels on third frame, causing pixels of illustration to be registered to a location on third frame corresponding to the location in field of view of illustration location in second frame. Alternatively, where offsite device 128 has registered illustration to field coordinate system as described above, augmented reality device 104 may register third frame to field coordinate system as described above; this may effect registration of pixels of illustration to third frame. Alternatively or additionally, where offsite device 128 identifies an object identifier of an object identified by processes described above, such as without limitation image classifier 140 process, augmented reality device 104 may detect an object identified by the object identifier, for instance using any object identification process as described above, and register the illustration to the object. In an embodiment, the above processes may be combined; for instance and without limitation, registration may be performed primarily using affine transformation, and checked using object detection. The above registration of illustration may be repeated with a plurality of subsequent frames. For instance, and without limitation, illustration may be registered to each frame of a plurality of subsequent frames until deleted by a command from onsite surgeon, offsite surgeon, and/or another user, until detection that an object associated with image as described above has changed, lapsing of a timeout set by default and/or as selected by onsite and/or offsite surgeon, such as a timeout after some number of seconds, and/or any other suitable reason FIG. 7 depicts an embodiment of third frame 700 with an illustration 704 added to indicate an anatomical feature.

In an embodiment, and still referring to FIG. 4, augmented reality device 104 may display 132 illustration to onsite surgeon. For instance, and without limitation, augmented reality device 104 may project illustration onto a field of vision of onsite surgeon, using projecting device. Illustration may be projected at pixel locations identified by registration of illustration to third frame. Augmented reality device 104 may project illustration onto field of vision with each registration of each subsequent frame to which illustration is registered. Alternatively or additionally, augmented reality device may project illustration onto operation locus; position of projected image may be determined based on registration to field coordinates. A grid as described above may be projected onto operation locus and/or displayed on a display and/or view window using projection device; display of grid and/or illustration, however accomplished, may be switched on or off in response to commands from onsite and/or offsite surgeon, including without limitation voice commands. Cessation of display of illustration may occur for any reason described above for cessation of registration.

Continuing to refer to FIG. 1, augmented reality device 104 and/or offsite device 128 may perform one or more error detection and/or correction processes. For instance, and without limitation, during initial registration of first frame, locations of one or more sets of reference coordinates may be registered, for instance by registering vertices of a frame of first frame to field coordinate system or the like. Distances between reference coordinates may be signaled to offsite device 128 by augmented reality device 104. Subsequently or concurrently any registration of one or more coordinates of interest by either offsite device 128 or augmented reality device 104 may be accompanied with computation, storage, and/or signaling of distances from each reference coordinate set to coordinates of interest, such as without limitation vertices of a frame indicated by a reference index, coordinates of objects such as operation locus and/or anatomical features, or the like. Checks for errors may include measuring distances between reference coordinates and each other and/or coordinates of interest, and comparison to signaled distances; any discrepancy may indicate that an error has been introduced. Error correction may be performed, for instance and without limitation, by a "majority rule" approach, whereby, for instance, if all numbers but one agree, then the disagreeing number may be changed to be consistent with the other numbers. For instance, if distances from reference coordinates to y and z coordinates of a coordinate set of interest are all as signaled while distances to x coordinate is not as signaled, the x coordinate may be treated as faulty and replaced with an x coordinate value consistent with the recorded distances. Offsite device 128 and/or augmented reality device 104 may count numbers in agreement, and where one set of internally consistent numbers is some threshold multiple of another set of internally consistent numbers, the latter may be changed to be consistent to the former; for instance, in the above example, the x coordinate was in a group of one number, and y and z coordinates as well as distances were all internally consistent, such that the latter set of internally consistent numbers was several times as large as the set containing the erroneous value of x. In an embodiment, registration of a frame may include identifying reference coordinates of some excess number of pixels to the minimal number needed to identify position of the frame within the coordinate system, such as identification of one pixel more, twice as many pixels, or ten times as many pixels. The above-described majority rule process for error correction may alternatively or additionally be used to detect errors in and/or correct stored data; for instance, lookup tables, transformation computations, and/or storage of vector and/or matrix values may be performed redundantly, for use in error detection and/or correction, as described in further detail below. Error correction and/or detection may be further supported by storage and/or transmission of data using parity checking techniques, one-hot or Gray coding, or the like.

Still referring to FIG. 4, where an error and/or failure is detected but not correctable, augmented reality device 104 and/or offsite device 128 may display 132 and/or otherwise output a warning message, and/or to engage one or more mitigation strategies; for instance and without limitation, detection of video failure may result in a data transmission indicating failure to either or both of onsite surgeon and offsite surgeon. Where video transmission failure has occurred, offsite surgeon may be provided by offsite device 128 with a still, such as a still selected as having high quality, that was previously received; such stills may be archived periodically for such purposes so that a relatively recent still may be used. Where other data transmission is possible, offsite surgeon may be able to perform some illustration and/or communication; for instance, still may be archived on augmented reality device 104 as well, such that illustrations may be signaled using an index of still, and thus reproduced on still by augmented reality device 104, and subsequently projected using projection device 112 to display 132 visual instruction.

Figure 8:
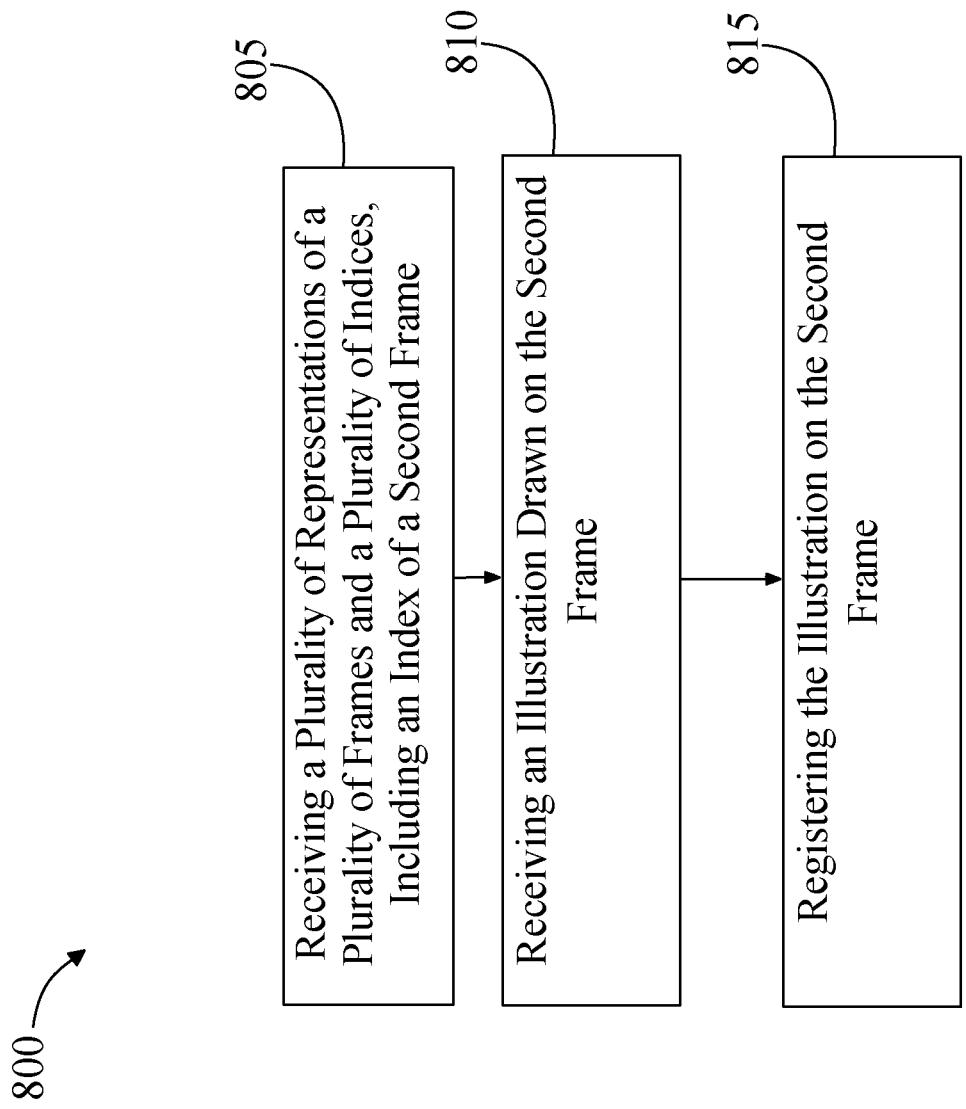
FIG. 8 is a flow diagram of an embodiment of a method for remote augmented reality communication for guided surgery.

Referring now to FIG. 8, an exemplary embodiment of a method 800 of remote augmented reality communication for guided surgery is illustrated. At step 805, an offsite device 128 receives, from an augmented reality device 104, a plurality of representations of the plurality of frames and a plurality of indices, each index corresponding to a frame of the plurality of frames, wherein the plurality of indices includes a second frame index identifying a second frame; this may be performed, without limitation, as described above in reference to FIG. 4. At step 810, offsite device 128 receives, from an offsite surgeon, an illustration drawn on second frame; this may be performed, without limitation, as described above in reference to FIG. 4. At step 815, offsite device 128 registers illustration on second frame of the plurality of frames; this may be performed, without limitation, as described above in reference to FIG. 4.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
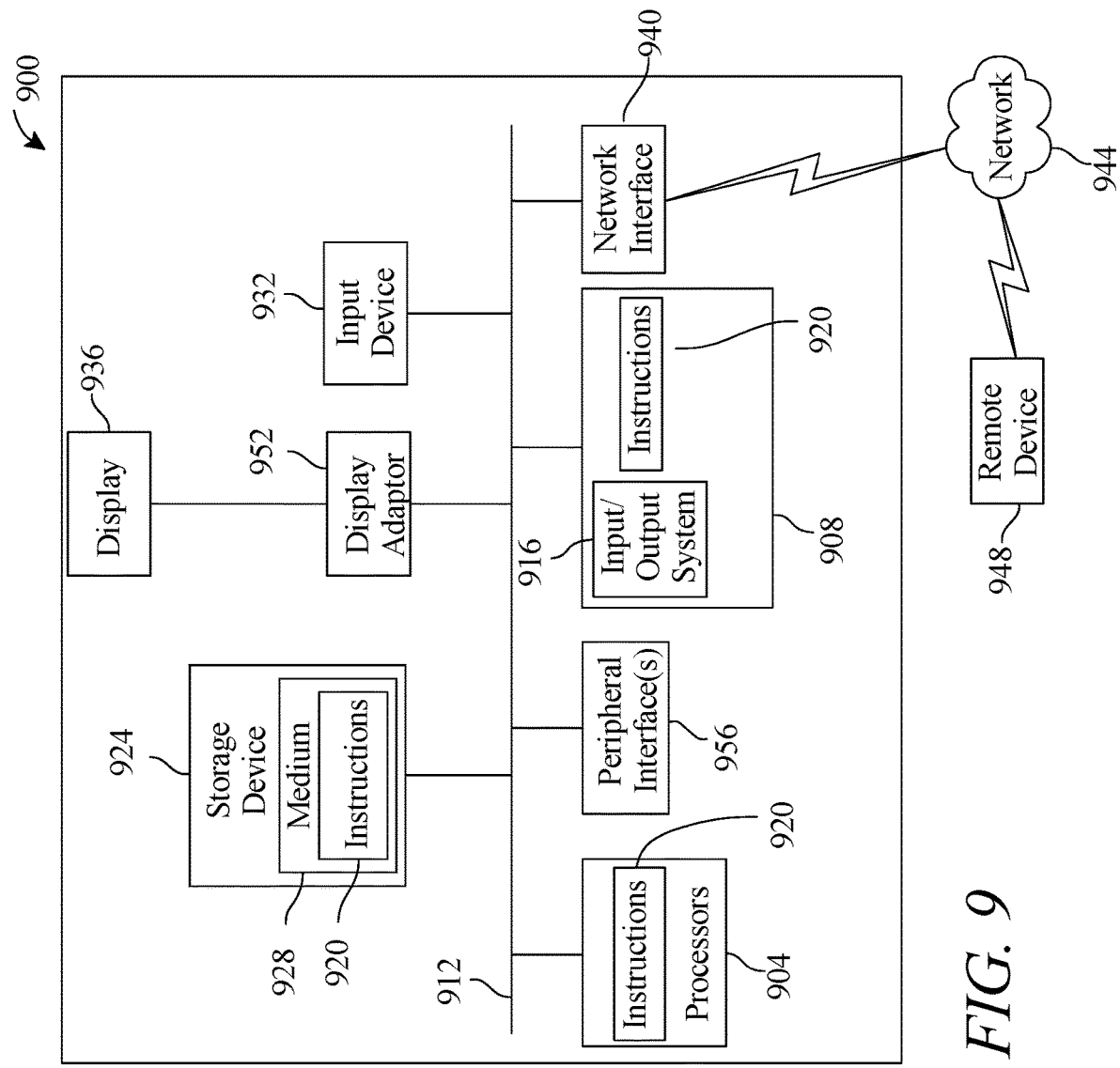
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor 124, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 132 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display 132 adapter 952 for communicating a display 132 able image to a display 132 device, such as display 132 device 936. Examples of a display 132 device include, but are not limited to, a liquid crystal display 132 (LCD), a cathode ray tube (CRT), a plasma display 132, a light emitting diode (LED) display 132, and any combinations thereof. Display 132 adapter 952 and display 132 device 936 may be utilized in combination with processor 904 to provide graphical representations of aspects of the present disclosure. In addition to a display 132 device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A method of remote augmented reality communication for guided surgery, the method comprising: receiving, by an offsite device, a plurality of representations of a plurality of frames and a plurality of indices, wherein the plurality of indices comprises at least a first frame index and at least a second frame index; displaying, by the offsite device and to an offsite surgeon, a second frame of the second frame index; inputting, by the offsite device, an illustration from the offsite surgeon, wherein the illustration is drawn on the second frame;
    registering, by the offsite device, the illustration to the second frame, wherein: registering produces registration data; and registering the illustration on the second frame comprises generating an object identifier as a function of an image classifier; and transmitting, by the offsite device, the illustration and the registration data.

2. The method of claim 1, wherein receiving the plurality of representations of the plurality of indices further comprises receiving each index of the plurality of indices wherein each index is configured to correspond to a frame of a plurality of frames.

3. The method of claim 1, wherein the receiving the plurality of representations of the plurality of frames and the plurality of indices further comprises a protocol, wherein the protocol is configured to transmit a video data of the plurality of frames from an augmented reality device.

4. The method of claim 1, wherein receiving the plurality of representations further comprises receiving data identifying a location within a field coordinate system of each pixel of the second frame.

5. The method of claim 1, wherein inputting the illustration of the second frame further comprises inputting the illustration using a locator device.

6. The method of claim 1, wherein registering the illustration on the second frame further comprises identifying a location within the field coordinate system of each pixel of the second frame.

7. The method of claim 6, wherein identifying the location within the field coordinate system comprises identifying the object identifier using an image classifier process.

8. The method of claim 1, wherein registering the illustration on the second frame further comprises determining an affine transformation from a first frame to the second frame.

9. The method of claim 8, wherein determining the affine transformation comprises transforming pixels of illustration of a first frame to pixels on the second frame.

10. An offsite device, the offsite device configured to: receive, by an augmented reality device, a plurality of representations of a plurality of frames and a plurality of indices, wherein the plurality of indices comprises at least a first frame index and at least a second frame index; display, by the offsite device and to an offsite surgeon, a second frame of the second frame index; input, by the offsite device, an illustration from the offsite surgeon,
    wherein the illustration is drawn on the second frame; register, by the offsite device, the illustration to the second frame, wherein registering produces registration data; and registering the illustration on the second frame comprises generating an object identifier as a function of an image classifier; and transmit, by the offsite device, the illustration and the registration data.

11. The system of claim 10, wherein receiving the plurality of representations of the plurality of indices further comprises receiving each index of the plurality of indices wherein each index is configured to correspond to a frame of a plurality of frames.

12. The system of claim 10, wherein the receiving the plurality of representation of the plurality of frames and the plurality of indices further comprises a protocol, wherein the protocol is configured to transmit a video data of the plurality of frames from an augmented reality device.

13. The system of claim 10, wherein receiving the plurality of representations further comprises receiving data identifying a location within the field coordinate system of each pixel of the second frame.

14. The system of claim 10, wherein the inputting the illustration of the second frame further comprises the offsite surgeon using a locator device.

15. The system of claim 10, wherein registering the illustration on the second frame further comprises identifying a location within the field coordinate system of each pixel of the second frame.

16. The system of claim 15, wherein identifying the location within the field coordinate system comprises identifying the object identifier by using an image classifier process.

17. The system of claim 10, wherein registering the illustration on the second frame further comprises determining an affine transformation from a first frame to the second frame.

18. The system of claim 17, wherein determining the affine transformation comprises transforming pixels of illustration of a first frame to pixels on the second frame.

19. An offsite device, the offsite device configured to: receive, by an augmented reality device, a plurality of representations of a plurality of frames and a plurality of indices, wherein the plurality of indices comprises at least a first frame index and at least a second frame index; display, by the offsite device and to an offsite surgeon, a second frame of the second frame index; input, by the offsite device, an illustration from the offsite surgeon, wherein the illustration is drawn on the second frame; register, by the offsite device, the illustration to the second frame, wherein registering produces registration data; and registering the illustration on the second frame further comprises determining an affine transformation from a first frame to the second frame; and transmit, by the offsite device, the illustration and the registration data.

* * * * *